US006815676B2

(12) United States Patent
Shirai et al.

(10) Patent No.: US 6,815,676 B2
(45) Date of Patent: Nov. 9, 2004

(54) MATERIAL DEFECT EVALUATION APPARATUS USING POSITRON AND ITS EVALUATION METHOD

(75) Inventors: Yasuharu Shirai, Kyoto (JP); Hideki Araki, Takarazuka (JP)

(73) Assignee: Osaka University, Osaka (JP)

( * ) Notice: Subject to any disclaimer, the term of this patent is extended or adjusted under 35 U.S.C. 154(b) by 0 days.

(21) Appl. No.: 10/606,485

(22) Filed: Jun. 26, 2003

(65) Prior Publication Data

US 2004/0075052 A1 Apr. 22, 2004

(30) Foreign Application Priority Data

Jun. 27, 2002 (JP) ........................................ 2002-187249

(51) Int. Cl.[7] .............................................. G01N 23/22
(52) U.S. Cl. ..................... 250/309; 250/307; 250/308
(58) Field of Search ................................ 250/309, 308, 250/307

(56) References Cited

U.S. PATENT DOCUMENTS

| 3,593,025 A | * | 7/1971 | Grosskreutz | ............. 250/358.1 |
| 2002/0030160 A1 | | 3/2002 | Greaves | |

FOREIGN PATENT DOCUMENTS

| JP | 05-288694 A1 | | 11/1993 | | |
| JP | 3448636 | * | 3/2001 | .......... | G01N/23/22 |
| JP | 2001-116706 A1 | | 4/2001 | | |

OTHER PUBLICATIONS

Barbieri, et al., "Nondestructive Positron–Lifetime Measurements During Fatigue of Austenitic Stainless Steel Using a Mobile Positron Beam," Applied Physics Letters, American Institute of Physics., NY, vol. 77, No. 12, Sep. 18, 2000, pp. 1911–1913, XP000964231.

* cited by examiner

Primary Examiner—John R. Lee
Assistant Examiner—James J. Leybourne
(74) Attorney, Agent, or Firm—Burr & Brown

(57) ABSTRACT

A material defect evaluation apparatus using positron for evaluating the degree of deterioration of a specimen by measuring a positron lifetime after irradiating positron to the specimen, includes: a positron source, a positron detector and a γ-ray detector, wherein, the positron source and the positron detector are arranged in a container through which a light is not transmitted, and, a positron transmitting window, through which position emanating from the positron source and transmitting through the positron detector is transmitted outward, is arranged to the container.

6 Claims, 2 Drawing Sheets

MATERIAL DEFECT EVALUATION APPARATUS USING POSITRON AND ITS EVALUATION METHOD

BACKGROUND OF THE INVENTION (1) Field of the Invention

The present invention relates to a material defect evaluation apparatus and its evaluation method, wherein a degree of deterioration of a specimen is evaluated by irradiating positron to the specimen and measuring a positron lifetime, and, especially relates to a material defect evaluation apparatus and its evaluation method, wherein a construction can be made compact and in situ non-destructive evaluation can be performed.

(2) Prior Art Statement

Positron has a weight equal to that of electron, and is a particle which has an electric charge equal to an absolute value of electric charge of electron and showing inverse positive and negative state. Positron is emitted from a radioisotope showing $\beta^+$ decay such as $^{22}$Na. If positron having an energy of several hundreds keV emitted from a positron source is irradiated to a specimen, positron is repeatedly crushed with electron and ion in the specimen, so that positron decays to a thermal energy level after a very short time such as 1 pico-second ($1\times10^{-12}$ second). The thus energy released positron, in the case that the specimen is metal, is annihilated with electron in a lifetime (specific to respective metals) such as about 100–300 pico-second. If there are defects such as vacant lattice points in the specimen, positron is trapped therein and is annihilated in a long lifetime specific to the defects (about 150–500 pico-second). Therefore, information regarding the defects can be obtained by measuring a lifetime in which positron is annihilated in the specimen.

As a method of measuring a positron lifetime, a sandwich method has been known. The radioisotope $^{22}$Na emits positron by $\beta^+$ decay. At that time, $\gamma$-ray having energy of 1.28 MeV is also emitted. On the other hand, when positron is annihilated with electron in the specimen, $\gamma$-ray having energy of 0.51 MeV is also emitted. Then, in order to measure a positron lifetime, two specimens are prepared that are made of the material whose positron lifetime is to be measured, and a ray source is sandwiched by the thus prepared two specimens, so that all the positron emitted from the ray source can be incident upon the specimens to be measured. Then, two $\gamma$-ray detectors are used in such a manner that one detects $\gamma$-ray having energy of 1.28 MeV so as to know a positron generation time and the other detects $\gamma$-ray having energy of 0.51 MeV so as to know a positron annihilation time, and a positron lifetime in the specimen is measured on the basis of a time difference between the positron generation time and the positron annihilation time. In this method, strictly speaking, the positron generation time is different from the positron incident time. However, if the ray source is arranged close to the specimen, it is possible to assume that the positron generation time is actually same as the positron incident time.

In the sandwich method mentioned above, it is necessary to use two specimens made of the same material. The reason is as follows. That is, if only one specimen is used, major part of positrons, whose generation time is known by detecting $\gamma$-ray having energy of 1.28 MeV, are annihilated in a material other than the specimen or in the atmosphere, and thus it is not possible to measure a positron lifetime of the specimen accurately. The measurement of positron lifetime can be theoretically performed in a non-destructive manner, but, at present, it is not possible to apply the measurement of positron lifetime for a non-destructive measurement of structural materials due to the limitations on measuring mentioned above. Moreover, even in a measurement on a laboratory, if the measurement of positron lifetime can be performed only by one specimen, it is possible to measure a precious specimen even though only one specimen exists in the world. In addition, even in normal specimens, it is possible to reduce a cost and save a trouble for preparing the specimens.

As a method of measuring a positron lifetime only by one specimen, there is disclosed a method wherein two positron lenses are used and positrons emitted from the ray source is converged by the two positron lenses and is incident upon the specimen (Yasuharu Shirai, et al J.Japan Inst. Metals, Vol. 59, No.6 (1995), pp. 679–680, and, Yasuharu Shirai: The production and technique, Vol. 48, No. 4 (1996), pp 50). In this method, a positron lifetime can be measured only by one specimen. However, since it is necessary to accommodate the specimen in a vacuum chamber, it is not possible to perform the measurement of positron lifetime for a large specimen. In addition, since it is necessary to use vacuum devices and electromagnetic lenses, there arises a drawback such that an apparatus is expensive.

Moreover, in the known method, in order to know the positron incident time, it is necessary to detect $\gamma$-ray having energy of 1.28 MeV, In addition, in order to pick-up a high-speed timing signal from $\gamma$-ray having high energy, it is necessary to use a high-speed scintillate and a high-speed photo-multiplier. Therefore, it is not possible to make a size of a start detector compact to a size of about 50 mm $\phi\times$ about 250 mm L under without decreasing time resolution. A stop detector has also the same drawback. Since it is necessary to use two large detectors such as the start detector and the stop detector mentioned above, it is almost impossible to apply this method to a non-destructive measurement.

SUMMARY OF THE INVENTION

An object of the invention is to eliminate the drawbacks mentioned above and to provide a material defect evaluation apparatus using positron and its evaluation method wherein a non-destructive in-situ measurement of a positron lifetime of a large structure can be performed effectively in a short period of time.

According to the invention, a material defect evaluation apparatus using positron for evaluating the degree of deterioration of a specimen by measuring a positron lifetime after irradiating positron to the specimen comprises: a positron source, a positron detector and a $\gamma$-ray detector, wherein, the positron source, and the positron detector are arranged in a container though which a light is not transmitted, and, a positron transmitting window, through which positron emanating from the positron source and transmitting through the positron detector is transmitted outward, is arranged to the container.

Moreover, according to the invention, an evaluation method using the material defect evaluation apparatus mentioned above, comprises the steps of: detecting a pass of positron emanating from the positron source by means of the positron detector; emitting positron through the positron transmitting window to the specimen; detecting a generation of $\gamma$-ray due to positron annihilated in the specimen by means of the $\gamma$-ray detector; measuring the positron lifetime defined by an interval between the time when the pass of positron is detected by means of the positron detector and the time when the generation of $\gamma$-ray is detected by means of the $\gamma$-ray detector; and evaluating material defects of the specimen on the basis of the thus measured positron lifetime.

In the sandwich method, a positron generation time is known by detecting $\gamma$-ray having energy of 1.28 MeV, and this positron generation time is assumed as a time when positron is incident upon the specimen to be measured. Therefore, a ray source is not arranged apart from the specimen, and thus the ray source must be arranged close to the specimen as much as possible. As a result, the specimen is always exposed in danger of deterioration due to the ray source. Moreover, since a direction, to which γ-ray having energy of 1.28 MeV is emitted, is not correlated with a direction, to which positron is emitted, it is not possible to specify positron emitting direction even if γ-ray having energy of 1.28 MeV is detected. Therefore, it is necessary to cover the ray source by the material of specimen to be measured, so as to annihilate all the positrons in the material of specimen even if positron is emitted in any directions. If positron incident upon the specimen can be directly detected and the directly detected positron incident time can be utilized as a positron generation time without using the positron generation time known from a generation time of γ-ray having energy of 1.28 MeV, it is not necessary to cover the ray source by the material of specimen as is the case of the sandwich method. After the above investigation, the present inventors have found the material defect evaluation apparatus using positron and its evaluation method.

BRIEF DESCRIPTION OF THE DRAWINGS

For a better understanding of the invention, reference is made to the attached drawings, wherein.

DETAILED DESCRIPTION OF THE INVENTION

Figure 1:
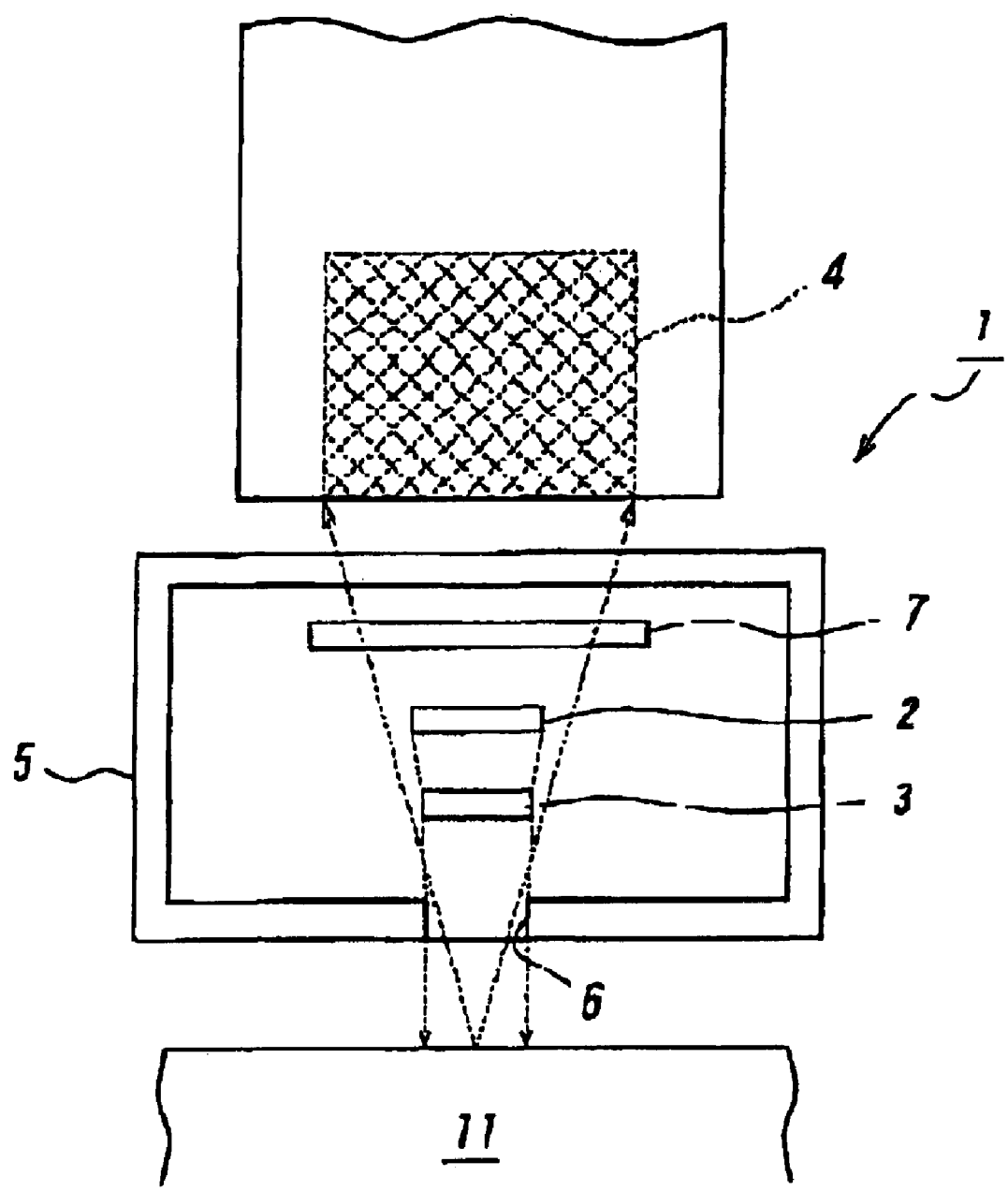
FIG. 1 is a schematic view showing one embodiment of a material defect evaluation apparatus using positron according to the invention.

FIG. 1 is a schematic view showing one embodiment of a material defect evaluation apparatus using positron according to the invention. In the embodiment shown in FIG. 1, a material defect evaluation apparatus 1 for evaluating the degree of deterioration of a material of specimen to be measured by irradiating positron to the specimen and measuring a lifetime of the irradiated positron comprises a positron source 2, a positron detector 3 and a γ-ray detector 4. Moreover, the positron source 2 and the positron detector 3 are arranged in a container 5 through which a light is not transmitted. In addition, a positron transmitting window 6, through which positron emanating from the positron source 2 and transmitting through the positron detector 3 is transmitted outward, is arranged to the container 5.

In the embodiment shown in FIG. 1, as a preferred embodiment, the γ-ray detector 4 is arranged outside of the container 5 at a position which is opposed to the positron detector 3 via the positron source 2. In addition, a positron shield 7, which is made of a material having a known positron lifetime that is not equal to a positron lifetime of the specimen to be measured, is arranged in the container 5 at a position which is opposed to the positron detector 3 via the positron source 2. Since the material defect evaluation apparatus 1 according to the invention having the construction mentioned above can be made compact in construction, it is possible to evaluate a degree of irradiation damage, fatigue and creep damage of a material of a material consisting of important equipment in nuclear reactor, jet engine, large power generation turbine and so on, in an in-situ non-destructive manner.

In the material defect evaluation apparatus 1 using positron according to the invention mentioned above, a material defect is evaluated as follows. At first, as shown in FIG. 1, the material defect evaluation apparatus is set near a specimen 11 to be measured. Then, a pass of positron emitted from the positron source 2 is detected by the positron detector 4. The thus detected time is assumed as a positron generation time. Then, positron transmitted through the positron transmitting window 6 is irradiated to the specimen 11, and a γ-ray generation due to positron annihilated in the specimen 11 is detected by the γ-ray detector 4. The thus detected time is assumed as a positron annihilation time. After that, a positron lifetime defined by a time interval between the positron generation time and the positron annihilation time is measured by a processing device not shown, and a defect of the specimen 11 is evaluated on the basis of the thus measured positron lifetime.

Figure 2:
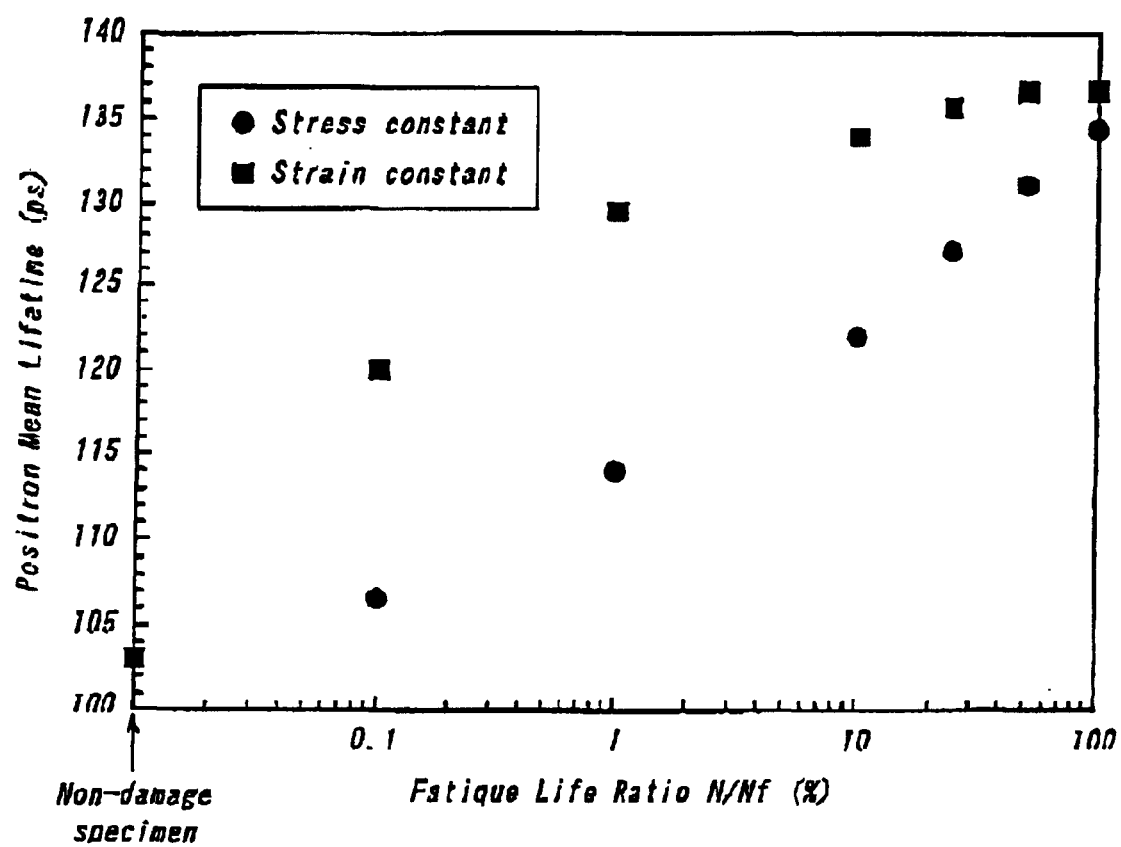
FIG. 2 is a graph illustrating a relation between a positron mean lifetime and a fatigue life ratio with respect to a stainless steel under constant stress or strain state.

A method for evaluating the material defect of the specimen 11 is the same as that of the known one. As one example, FIG. 2 is a graph showing a relation between a positron mean lifetime and a fatigue life ratio (N/Nf) of stainless steel for a stress constant specimen and a strain constant specimen. In the graph shown in FIG. 2, the fatigue life ratio (N/Nf): 0% shows a data of non-damage specimen, and the fatigue life ratio: 100% depicts a data of fracture specimen. From the results shown in FIG. 2, it is understood that, if the positron lifetime is measured, a current state of the specimen 11, i.e., how long a lifetime of the specimen will be, can he evaluated on the basis of the thus measured positron lifetime.

Hereinafter, respective members of the material defect evaluation apparatus 1 according to the invention will be explained in detail. At first, as the positron source 2, use is made of a radioisotope which emits positron by $\beta^+$ decay, i.e., $^{22}$Na or $^{68}$Ge. Such positron emitted from the radioisotope has normally a kinetic energy about 300–800 keV, and transmits easily through a metal foil having a thickness of about 0.01 mm. The positron transmitting window 6 has a sufficiently thin thickness so as to transmit positron therethrough and also has a sufficient strength so as not to be fractured. Therefore, as the positron transmitting window 6, it is preferred to use the metal foil such as beryllium foil, titanium foil, nickel foil and so on each having a thickness of about 0.01 mm.

As the position detector 3 for detecting a pass of positron and also transmitting positron therethrough, use is made of a silicon avalanche photodiode having a thickness of about 0.1 mm. In this case, since the positron, it detects positron but at the same time detects lights other than positron, it is necessary to accommodate the positron detector 3 in the container 5 through which lights are not transmitted, for shielding the positron detector 3 from lights. Moreover, a part of positrons incident upon the positron detector 3 is scattered in the positron detector 3 and is returned backward. One part of the thus scattered positrons is annihilated in the positron source 2, and the other part thereof is transmitted through the positron source 2 and is incident upon the container 5 arranged backward with respect to the positron source 2. When such positron incident upon the backward container 5 is annihilated, γ-ray is generated as a noise. Therefore, it is preferred to arrange the positron shield member 7 made of a material whose positron lifetime has been known and is not equal to that of the specimen 11 to be measured, at a backward position of the positron source 2. If such material is selectively used for the positron shield member 7, it is possible to correct signals on the basis of its known positron lifetime. Moreover, if normal metals are used for the positron shield member 7, it is sufficient to make a thickness thereof to about 1 mm. Of course, it is possible to add a light shielding function to the container 5 by using the same material as that of the positron shield member 7 for the container 5.

In order to irradiate all positrons transmitted through the positron detector 3 to the specimen 11, except for the positron whose moving direction is largely varied by the scattering in the positron detector 3, it is preferred to make an area of the positron transmitting window 6 larger than an effective area of the positron detector 3 and to arrange the positron transmitting window 6 close to the positron detector 3. In this embodiment, positron emitted from the positron transmitting window 6 is irradiated to the specimen 11, and γ-ray due to the positron annihilation in the specimen 11 is detected by the γ-ray detector 4. In this case, in order to make a solid angle for trapping γ-ray larger, it is preferred to arrange, the γ-ray detector 4 just above a position where positron is irradiated to the specimen 11, i.e., at a position which is opposed to the positron detector 3 via the positron source 2. Since γ-ray has a large transmissivity, there is almost no loss of γ-ray even if the positron source 2, the positron shield member 7 and the positron detector 3 are sandwiched between the γ-ray detector 4 and the specimen 11. Moreover, since the γ-ray detector 4 detects also visible ray, it is normally used under a light shielding condition. Therefore, the γ-ray detector 4 may be arranged in the container 5 having a light shielding function together with the positron detector 5, and the container 5 may be used for shielding the γ-ray detector 4 from light.

In the γ-ray detector 4, γ-ray which is scattered backward with respect to the positron detector 3 and is annihilated in the positron source 2 or in the positron shielding member 7 arranged backward with respect to the positron source 2, and, γ-ray which is not incident upon the positron detector 4 and is generated due to positron annihilated in the positron source 2 or in the container 5, are detected other than γ-ray (which is a signal to be measured) which is passed through the positron detector 3 and is generated due to the annihilated positron in the specimen 11. An affection of γ-ray which is not incident upon the positron detector 4 and is generated due to positron annihilated in the positron source 2 or in the container 5 can be decreased if use is made of a weak positron source 2 as mentioned below.

Generally, since position lifetime is in a range from 100 pico-seconds to several nano-seconds in a material, it is preferred to use a weak positron source 2 so as not to generate another positron in a time interval of several nano-seconds wherein one positron is transmitted through the positron detector 3 and is annihilated. For example, in a ray source with 10 microcurie, the number, of positrons emitted is 360 thousands per second, and thus one positron is emitted about every 3 micro seconds. If a signal is measured only in the case wherein γ-ray is emitted within 10 nano-seconds from a time at which positron is detected by the positron detector 3, it is possible to make a ratio under 1/300 between a signal of γ-ray generated due to positron which is transmitted through the positron detector 3 and is annihilated in the specimen 11 and a signal of γ-ray generated due to another positron which is accidentally generated within 10 nano-seconds from a time at which positron is detected by the positron detector 3. In this case, even if the weak positron source 2 is used, 360 thousands per second of positrons are generated. Therefore, if only the number of positrons transmitted through the position detector 3 is measured, it is possible to obtain easily a signal such as 100 counts per second as measured by the known sandwich method.

As to a signal of γ-ray which is once incident upon the positron detector 3, scattered backward in the positron detector 3 and annihilated in the positron source 2 or in the container 5 arranged backward with respect to the positron source 2, it is possible to reduce it by making a thickness of the positron detector 3 thin. In addition, as mentioned above for the positron shield member 7, it is possible to perform a correction of the signal by selecting a material whose positron lifetime is not equal to that of the specimen 11 for a material of the container 5 and subtracting a part corresponding to the positron lifetime of the container 5 from the signal.

Hereinafter, a function of respective members consisting of the material defect evaluation apparatus 1 according to the invention will be explained. At first, the reason for using preferably the avalanche photodiode for the positron detector 3 is that it is possible to detect positron with almost 100% accuracy even if a thickness of the positron detector 3 is made thin to about 0.1 mm so as to transmit positron therethrough. As a result, as compared with the known method, it is possible to reduce a volume of the positron detector 3 by almost thousandth. Moreover, the reason for accommodating the positron detector 3 in the light shielding container 5 is that, if not so, a signal (noise) is generated by detecting an outer light by the positron detector 3. Further, it is not always necessary to accommodate the positron source 2 in the light shielding container. However, in order to irradiate positron emitted from the positron source 2 to the positron detector 3, it is effective to accommodate both of the positron source 2 and the positron detector 3 in the same container 5. Furthermore, the reason for using preferably the metal foil for the positron transmitting window 6 is that the metal foil can be made thin to a level under 0.01 mm so as to transmit positron therethrough and also has a strength so as not to be easily fractured. As such metal foil materials, nickel, beryllium, titanium, aluminum and so on are used suitably. Moreover, the reason for arranging preferably the γ-ray detector 4 at a position which is opposed to the specimen 11 via the positron source 2 is that it is possible to make an effective angle for measuring γ-ray larger.

Hereinafter, an actual example will be explained.

In the material defect evaluation apparatus 1 according to the invention having the construction shown in FIG. 1, the positron source 2 made of $^{22}$Na having strength of 10 microcurie was screwed between two aluminum plates. A hole having a diameter of 4 mm was formed at a center portion of one plate, and the avalanche photodiode as the positron detector 3 was fixed near the hole. A size of an effective detection portion of the avalanche photodiode was 5 mm×5 mm, and all positions, which were emitted from the positron source 2 and transmitted through the positron transmitting window 6, were incident upon the effective detection portion of the avalanche photodiode. A thickness of the effective detection portion of the avalanche photodiode was 0.1 mm, and thus almost all positrons were transmitted therethrough. The positron source 2 and the avalanche photodiode were accommodated in the container 5 made of stainless steel having a thickness of 1 mm, to which the positron transmitting window 6 made of titanium foil having a diameter of 10 mm and a thickness of 0.03 mm. The container 5 made of stainless steel was designed in such a manner that a light was not transmitted. In this embodiment, positron was emitted from the position source 2 and transmitted through the positron transmitting window 6 made of titanium foil, so that positron was introduced outside of the container 5. As the γ-ray detector 4, the photo-multiplier with BaF$_2$ scintillate was used and fixed at a position that was outside of the container 5 made of stainless steel and just above the positron source 2.

A specimen made of pure iron having a dimension of 30 mm×30 mm×1 mm was formed and was annealed at 600° C. for 1 hour. Then, a surface oxidized film of the specimen was removed by electrolytic polishing, and the positron lifetime was measured by means of the material defect evaluation apparatus 1 according to the invention. A signal due to γ-ray annihilation was 300 counts par second, and data of one million counts was obtained after measurement for 60 minutes. In the case that the material defect evaluation apparatus 1 according to the invention was used, it was supposed that a part of positrons was annihilated in the avalanche photodiode and that another part of positrons was scattered in the avalanche photodiode to vary its moving direction, incident upon the positron source 2 again and annihilated in the positron source 2 or in the container 5 after positron clash with respect to the container 5 through the positron source 2. As a result, it is supposed that a component part corresponding to the positron lifetime of silicon or stainless steel was included in the signal. The positron lifetime in the positron source 2 was 350 pico-seconds, and the positron lifetimes of silicon and stainless steel were about 200 pico-seconds respectively. Since the positron lifetime of pure iron having little defects was known to be 105 pico-seconds, it is possible to perform a performance evaluation of the material defect evaluation apparatus according to the invention by measuring the positron lifetime of the specimen made of pure iron and investigating a component part corresponding to the positron lifetime of 105 pico-seconds. The thus obtained data of the positron annihilation was analyzed by three compound parts corresponding to the positron lifetimes of 105 pico-seconds. 200 pico-seconds and 350 pico-seconds, and a strength ration was measured. The results were shown in the following Table 1.

From the results shown in Table 1, it is understood that the component part of 105 pico-seconds showing the positron lifetime of pure iron is measured by 55% and thus an accurate position lifetime of the specimen can be measured Moreover, the component part of 200 pico-seconds is included by 20% and the component part of 350 pico-seconds is included by 25%. This is due to the positron annihilations in the avalanche photodiode and the positron source 2. These affections can be reduced by removing previously these component parts when performing the measurement.

Then, as a comparison, a positron lifetime of the same specimen made of pure iron as mentioned above was measured in such a manner that the positron source of 10 microcurie was sandwiched by stainless steel plates and two γ-ray detectors were used. As the γ-ray detectors, use was made of the same photo-multiplier with $BaF_2$ scintillater as mentioned above, and were arranged with an angle of 45° and backward with respect to the stainless steel plate. The reason for arranging the two γ-ray detectors backward with respect to the stainless steel plate was that the γ-ray detector was not arranged backward with respect to the specimen when measuring large specimen (such as boiler pipe for power generation). As the positron source, use was made of $^{22}$Na having 10 microcurie. The results were shown in the following Table 1. In this case, a signal due to γ-ray annihilation was 30 counts per second. Moreover from the results shown in Table 1, it is understood that a strength ratio of the component part of 105 pico-seconds that is a proper signal is 40% and that, on the other hand, the component part of 200 pico-seconds is 40% and the component part of 350 pico-seconds is 20%.

From the results mentioned above, it is confirmed that the present invention can measure a large signal and a large strength ratio of the measured signal, as compared with the known sandwich method.

TABLE 1

| Present invention | Measurement rate: 300 counts per second<br>Component part of 105 pico-seconds: 55%<br>Component part of 200 pico-seconds: 20%<br>Component part of 350 pico-seconds: 25% |
|---|---|
| Sandwich method | Measurement rate: 30 counts per second<br>Component part of 105 pico-seconds: 40%<br>Component part of 200 pico-seconds: 40%<br>Component part of 350 pico-seconds: 20% |

As is clearly understood from the above explanations, according to the invention, since there are a positron source, a positron detector and a γ-ray. detector, wherein, the positron source and the positron detector are arranged in a container through which a light is not transmitted, and, a positron transmitting window, through which positron emanating from the positron source and transmitting through which positron detector is transmitted outward, is arranged to the container, it is possible to make an apparatus construction compact, and thus a non-destructive in-situ measurement of a positron lifetime of a large structure can be performed effectively in a short period of time.

What is claimed is:

1. A material defect evaluation apparatus using positrons for evaluating the degree of deterioration of a specimen by measuring a positron lifetime after irradiating the specimen with positrons, said apparatus comprising:
   a positron source,
   a positron detector and
   a gamma ray detector,
   wherein said positron source and said positron detector are arranged in a container through which light is not transmitted, said container comprising a positron-transmitting window and
   wherein positrons emitted from said positron source that are transmitted through said positron detector are irradiated onto a specimen that is disposed outside said container.

2. The material defect evaluation apparatus using positron according to claim 1, wherein the γ-ray detector is arranged outside of the container at a position which is opposed to the position detector via positron source.

3. The material defect evaluation apparatus using positron according to claim 1, wherein a positron shield member, which is made of a material having a known positron lifetime that is not equal to a positron lifetime of the specimen, is arranged in the container at a position which is opposed to the positron detector via the positron source.

4. The material defect evaluation apparatus using positron according to claim 1, wherein a metal film is used as the positron transmitting window.

5. The material defect evaluation apparatus using positron according to claim 1, wherein the positron detector is an avalanche photo diode.

6. An evaluation method using the material defect evaluation apparatus set forth in one of claims 1–5, comprising the steps of: detecting a pass of positron emanating from the from the positron source by means of the positron detector; emitting positron through the positron transmitting window to the specimen; detecting a generation of γ-ray due to positron annihilated in the specimen by means of the γ-ray detector, measuring the position lifetime defined by an interval between the time when the pass of positron is detected by means of the positron detector and the time when the generation of γ-ray is detected by means of the γ-ray detector, and evaluating material defects of the specimen on the basis of the thus measured positron lifetime.

* * * * *